(12) United States Patent
Nakatani et al.

(10) Patent No.: US 7,931,934 B2
(45) Date of Patent: Apr. 26, 2011

(54) MEDICAL DEVICE HAVING DIAMOND-LIKE THIN FILM AND METHOD FOR MANUFACTURING THEREOF

(75) Inventors: Tatsuyuki Nakatani, Hiroshima (JP); Keishi Okamoto, Hiroshima (JP); Shuzo Yamashita, Okayama (JP); Koji Mori, Okayama (JP); Ikuo Komura, Okayama (JP)

(73) Assignees: Toyo Advanced Technologies Co., Ltd., Hiroshima-shi (JP); Japan Stent Technology Co., Ltd., Okayama (JP)

( * ) Notice: Subject to any disclaimer, the term of this patent is extended or adjusted under 35 U.S.C. 154(b) by 55 days.

(21) Appl. No.: 12/301,003

(22) PCT Filed: Jan. 15, 2007

(86) PCT No.: PCT/JP2007/050416
§ 371 (c)(1),
(2), (4) Date: Nov. 14, 2008

(87) PCT Pub. No.: WO2007/132570
PCT Pub. Date: Nov. 22, 2007

(65) Prior Publication Data
US 2009/0209942 A1    Aug. 20, 2009

(30) Foreign Application Priority Data
May 17, 2006   (JP) ................................. 2006-138246

(51) Int. Cl.
*B05D 3/00*   (2006.01)
*H01L 29/15*   (2006.01)
*A61F 2/06*   (2006.01)

(52) U.S. Cl. .......................... 427/2.25; 257/77; 623/1.15
(58) Field of Classification Search ........ 623/1.15–1.48; 428/216; 257/77; 250/288; 427/2.25
See application file for complete search history.

(56) References Cited

U.S. PATENT DOCUMENTS

| | | | |
|---|---|---|---|
| 5,250,149 A * | 10/1993 | Kimoto et al. ................. 117/97 |
| 5,352,493 A * | 10/1994 | Dorfman et al. ............. 427/530 |
| 5,541,003 A | 7/1996 | Nakayama et al. |
| 6,228,471 B1 * | 5/2001 | Neerinck et al. ............. 428/216 |
| 6,572,651 B1 * | 6/2003 | De Scheerder et al. ...... 623/1.44 |
| 7,391,018 B2 * | 6/2008 | Niu et al. ....................... 250/288 |
| 7,695,731 B2 * | 4/2010 | Falotico et al. .............. 424/425 |
| 2003/0069632 A1 * | 4/2003 | De Scheerder et al. ...... 623/1.15 |
| 2005/0113767 A1 * | 5/2005 | Palasis et al. ................. 604/264 |
| 2006/0142853 A1 * | 6/2006 | Wang et al. .................. 623/1.46 |
| 2007/0207321 A1 * | 9/2007 | Abe et al. ...................... 428/413 |
| 2007/0269936 A1 * | 11/2007 | Tanaka et al. ................. 438/133 |
| 2007/0284255 A1 * | 12/2007 | Gorokhovsky et al. ......... 205/89 |
| 2009/0005862 A1 * | 1/2009 | Nakatani et al. ............. 623/1.49 |
| 2009/0011252 A1 * | 1/2009 | Stein et al. .................... 428/446 |
| 2009/0012525 A1 * | 1/2009 | Buehlmann et al. ........... 606/92 |

(Continued)

FOREIGN PATENT DOCUMENTS

JP    63-286334 A    11/1988

(Continued)

*Primary Examiner* — Suzette J Gherbi
(74) *Attorney, Agent, or Firm* — Birch, Stewart, Kolasch & Birch, LLP

(57) ABSTRACT

A medical device includes a medial device body, and a diamond-like thin film covering the medical device body and containing silicon. The diamond-like thin film has a concentration of silicon which is lower in a surface thereof than in an interface thereof with the medical device body mentioned above, and continuously varies.

29 Claims, 6 Drawing Sheets

U.S. PATENT DOCUMENTS

| | | |
|---|---|---|
| 2010/0098964 A1 * | 4/2010 | Ruebig .................. 428/547 |
| 2010/0219418 A1 * | 9/2010 | Sung ..................... 257/77 |

FOREIGN PATENT DOCUMENTS

| JP | 5-124875 A | 5/1993 |
|---|---|---|
| JP | 11-313884 A | 11/1999 |
| JP | 2000-176705 A | 6/2000 |
| JP | 2001-29447 A | 2/2001 |
| JP | 2001029447 A * | 2/2001 |
| JP | 2001064276 A * | 3/2001 |
| JP | 2001-238962 A | 9/2001 |
| JP | 2003-310744 A | 11/2003 |
| JP | 2006-521 A | 1/2006 |
| WO | WO 2007132570 A1 * | 11/2007 |

* cited by examiner

FIG.2
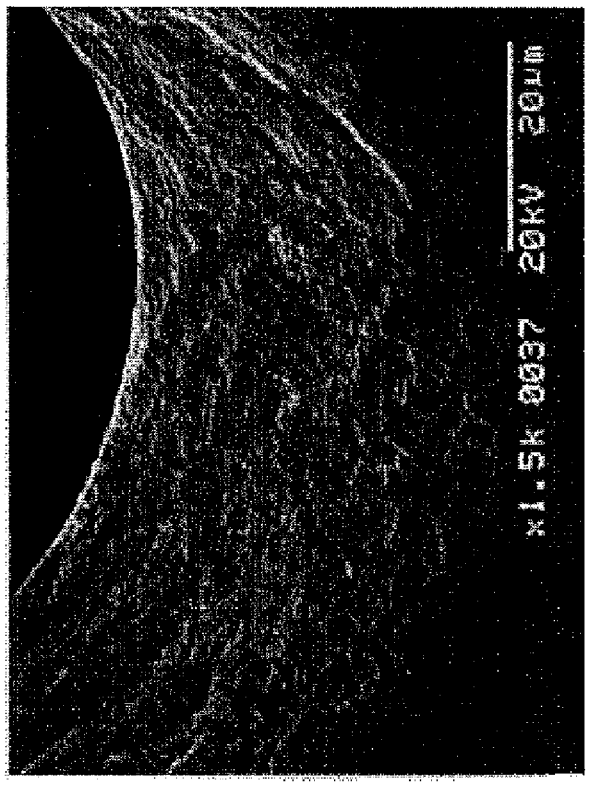
(b)
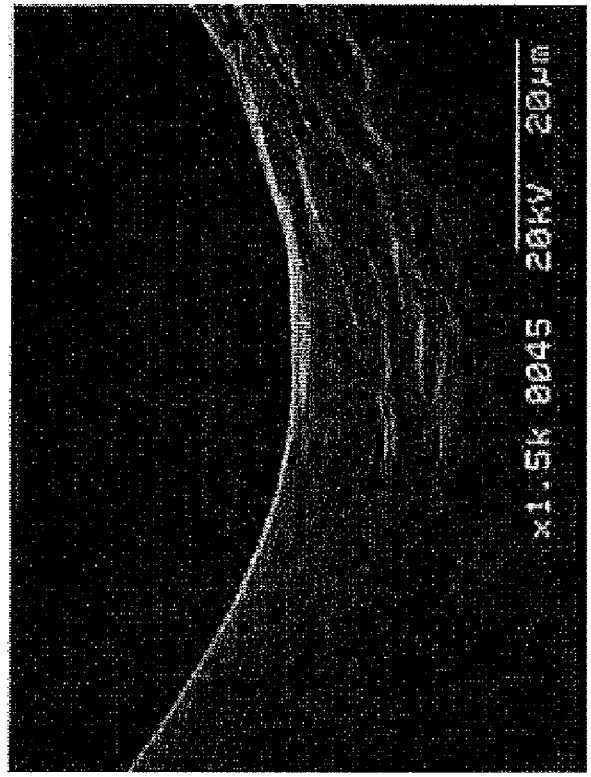
(a)

MEDICAL DEVICE HAVING DIAMOND-LIKE THIN FILM AND METHOD FOR MANUFACTURING THEREOF

TECHNICAL FIELD

The present invention relates to a medical device having a diamond-like thin film and a method for manufacturing thereof and, more particularly, to a medical device of which biocompatibility, abrasive resistance, and corrosive resistance are required and a method for manufacturing thereof.

BACKGROUND ART

An in-vivo indwelling medical device such as a catheter, a guide wire, a stent, a pacemaker lead, or an injection needle is in direct contact with a human body tissue, blood, and the like over a long period of time so that, not only biocompatibility such as an anti-thrombotic property, but also abrasive resistance, corrosive resistance, and the like are required.

As a method for imparting biocompatibility, corrosive resistance, and the like to a medical device, there is known a method which covers the base material of the medical device with a diamond-like thin film (DLC film) (see, e.g., Patent Document 1). Because the DLC film has a smooth surface which is chemically inactive, it is less reactive to a biological component, and shows excellent biocompatibility. The DLC film is also a hard material and excellent in abrasive resistance.

However, because of its low adhesion to the base material, the DLC film has the problem of delamination from the surface of the medical device. In particular, a stent or the like needs to perform expansion and contraction in a human body so that the shape thereof significantly changes. As a result, a large stress is added also to the DLC film covering the surface so that the DLC film delaminates or a crack occurs therein.

As a method for improving the adhesion between the DLC film and the base material of the medical device, and suppressing the delamination of the DLC film, there are known a method which forms an intermediate layer between the DLC film and the base material (see, e.g., Patent Document 2), and a method which forms a region having a large number of graphite bonds (SP2 bonds) on the side closer to the base material by adjusting conditions for generating a plasma (see, e.g., Patent Document 3).

Patent Document 1: Japanese Laid-Open Patent Publication No. HEI 11-313884
Patent Document 2: Japanese Laid-Open Patent Publication No. 2006-000521
Patent Document 3: Japanese Laid-Open Patent Publication No. 2003-310744

DISCLOSURE OF THE INVENTION

Problems to be Solved by the Invention

However, even though the conventional method which provides the intermediate layer mentioned above is used, the DLC film is invariably formed hard and low in adhesion. This leads to the problem that the occurrence of delamination and a crack cannot be sufficiently suppressed.

On the other hand, when the region having a large number of graphite bonds is formed on the side closer to the base material, the intrinsic properties of the DLC film change, and therefore it may be possible to suppress the occurrence of delamination and a crack. However, there is the problem that, even when the conditions for generating a plasma are adjusted, the ratio between the SP2 bonds and SP3 bonds cannot be sufficiently changed, and it is difficult to form a DLC film having both adhesion and abrasive resistance.

An object of the present invention is to solve the conventional problems described above, and allow the implementation of a medical device formed with a diamond-like thin film having both excellent adhesion which prevents the delamination thereof from the surface of the base material of a medical device over a long period of time and excellent abrasive resistance which renders the surface thereof less susceptible to degradation.

Means for Solving the Problems

To solve the problems described above, the present invention provides a medical device with a structure including a diamond-like thin film containing silicon such that the concentration thereof varies with distance from the interface of the diamond-like thin film with a base material toward the surface thereof.

Specifically, a medical device according to the present invention includes: a medial device body; and a diamond-like thin film covering the medical device body and containing silicon, wherein the diamond-like thin film has a concentration of the silicon which is lower in a surface thereof than in an interface thereof with the medical device body, and continuously varies.

In the medical device of the present invention, the diamond-like thin film has the silicon concentration which is lower in the surface thereof than in the interface thereof with the medical device body so that the ratio of the graphite bonds (SP2 bonds) is higher in the interface with the medical device body, while the ratio of the diamond bonds (SP3 bonds) is higher in the surface. Therefore, it is possible to provide compatibility between an improvement in adhesion at the interface with the medical device body and improvements in abrasive resistance, corrosive resistance, and anti-thrombotic property at the surface. In addition, since the silicon concentration continuously varies, a discontinuous surface is not formed within the diamond-like thin film. As a result, unlike in the case where a plurality of diamond-like thin films layers having different silicon concentrations are formed, there is no possibility of the occurrence of delamination between the layers.

In the medical device of the present invention, the diamond-like thin film preferably has an atomic percent concentration of the silicon which is not more than 50% in a portion thereof having the highest silicon concentration. With such an arrangement, it is possible to reliably ensure adhesion to the medical device body or the like, and the abrasive resistance of the surface. In this case, the diamond-like thin film preferably has the silicon concentration which is highest in the interface thereof with the medical device body.

Preferably, the diamond-like thin film has the silicon concentration in the surface thereof which is not more than 90% of the silicon concentration in the portion thereof having the highest silicon concentration.

In the medical device of the present invention, the diamond-like thin film preferably has an elastic modulus which is larger in the surface thereof than in the interface thereof with the medical device body.

In this case, the diamond-like thin film preferably has the elastic modulus which is not less than 50 GPa and not more than 400 GPa in the surface thereof.

In the medical device of the present invention, the diamond-like thin film preferably has graphite bonds and diamond bonds, and an abundance ratio of the graphite bonds to the diamond bonds is lower in the surface of the diamond-like thin film than in the interface thereof with the medical device body.

In the medical device of the present invention, the diamond-like thin film preferably contains fluorine, and preferably has a concentration of the fluorine which is higher in the surface thereof than in the interface thereof with the medical device body, and continuously varies. Such an arrangement increases the hydrophobic property of the surface of the diamond-like thin film to allow a further improvement in anti-thrombotic property or the like.

In this case, the diamond-like thin film preferably has an atomic percent concentration of the fluorine which is not less than 1% and not more than 20% in the surface thereof.

In the medical device of the present invention, the diamond-like thin film preferably has a film thickness which is not less than 5 nm and not more than 300 nm.

In the medical device of the present invention, the medical device body preferably has an arithmetical mean surface roughness which is not less than 0.1 nm and not more than 300 nm in a surface thereof.

In the medical device of the present invention, the medical device body is preferably a composite made of one or two or more of a metal material, a ceramics material, and a polymer material.

In the medical device of the present invention, the metal material is preferably stainless steel, a cobalt-chromium alloy, a titanium alloy, or a cobalt alloy.

In the medical device of the present invention, the medical device body is preferably a stent, a catheter, a guide wire, a pacemaker lead, in-vivo indwelling equipment, an injection needle, a scalpel, a vacuum blood collection tube, an infusion bag, a prefilled syringe, or a wound protector.

A method for manufacturing a medical device according to the present invention includes the steps of: (a) preparing a medial device body; and (b) forming a diamond-like thin film containing silicon on a surface of the medical device body, wherein, in the step (b), the diamond-like thin film is formed to have a concentration of silicon which is lower in a surface thereof than in an interface thereof with the medical device body, and continuously varies.

In accordance with the method for manufacturing a medical device of the present invention, the diamond-like thin film is formed to have the silicon concentration which is lower in the surface thereof than in the interface thereof with the medical device body, and continuously varies. Therefore, it is possible to easily implement a medical device having a DLC film which provides compatibility between an improvement in adhesion at the interface with the medical device body and improvements in abrasive resistance, corrosive resistance, and anti-thrombotic property at the surface.

In the method for manufacturing a medical device of the present invention, in the step (b), the diamond-like thin film is preferably formed to have an atomic percent concentration of the silicon which is not more than 50% in a portion thereof having the highest silicon concentration.

In this case, in the step (b), the diamond-like thin film is preferably formed to have the silicon concentration which is highest in the interface thereof with the medical device body.

In the step (b), the diamond-like thin film is preferably formed to have the silicon concentration in the surface thereof which is not more than 90% of the silicon concentration in the portion thereof having the highest silicon concentration.

In the method for manufacturing a medical device of the present invention, in the step (b), the diamond-like thin film is preferably formed to have an elastic modulus which is larger in the surface thereof than in the interface thereof with the medical device body.

In the method for manufacturing a medical device of the present invention, in the step (b), the diamond-like thin film is preferably formed to have graphite bonds and diamond bonds such that an abundance ratio of the graphite bonds to the diamond bonds is lower in the surface of the diamond-like thin film than in the interface thereof with the medical device body.

In the method for manufacturing a medical device of the present invention, in the step (b), the diamond-like thin film is preferably formed to contain fluorine, and have a concentration of the fluorine which is higher in the surface thereof than in the interface thereof with the medical device body, and continuously varies.

Effect of the Invention

In accordance with the present invention, it is possible to implement a medical device having both excellent adhesion which prevents delamination from the surface of the base material of the medical device over a long period of time and excellent abrasive resistance which renders the surface less susceptible to degradation.

BRIEF DESCRIPTION OF THE DRAWINGS

FIGS. 2(a) and 2(b) are electron microscopic photographs showing for comparison the surface of the DLC film of the stent according to the first embodiment of the present invention and the surface of the DLC film of a stent according to a comparative example;

FIGS. 5(a) and 5(b) show the result of measuring the abundance ratio of SP2 bonds to SP3 bonds in the DLC film of the stent according to the first embodiment of the present invention, of which FIG. 5(a) shows a Raman spectrum at the surface thereof, and FIG. 5(b) shows a Raman spectrum at the interface thereof with a stent body.

DESCRIPTION OF NUMERALS

Figure 1:
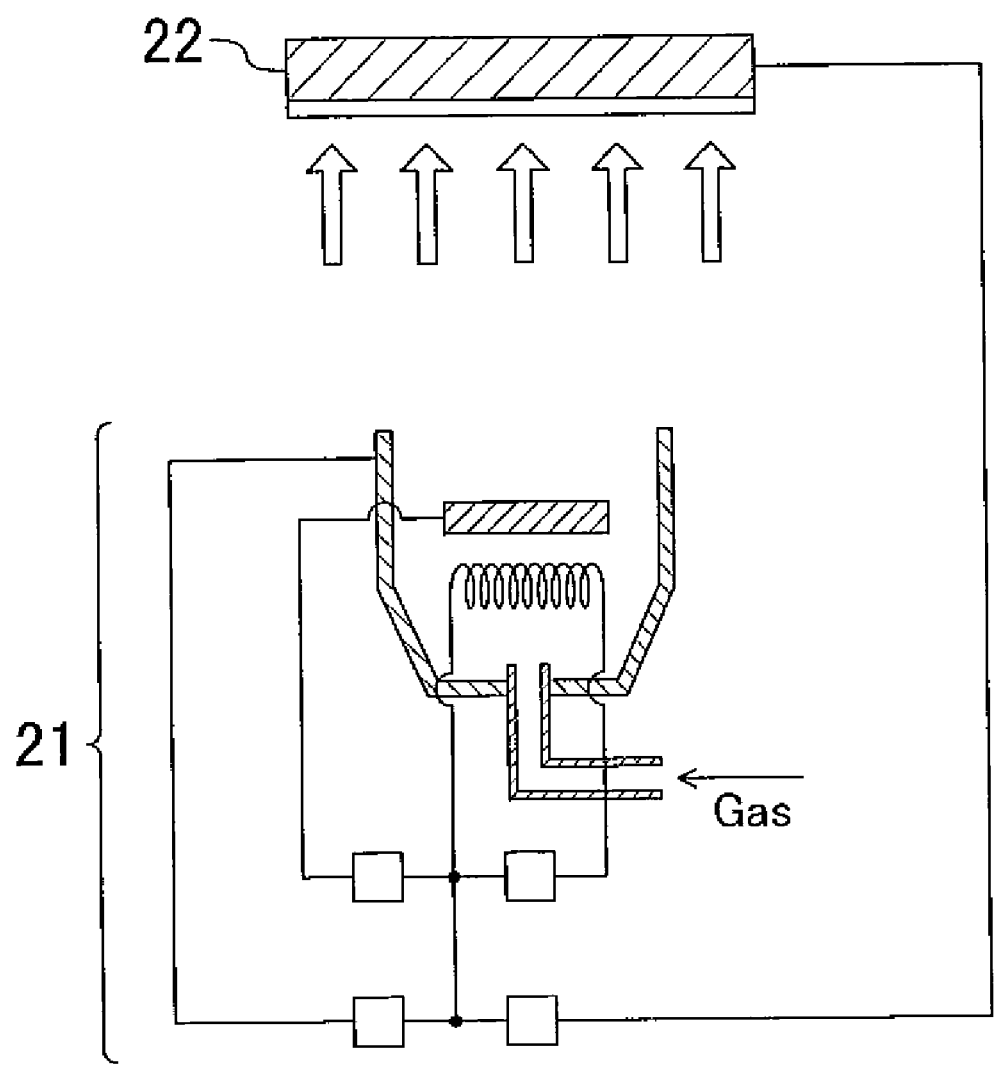
FIG. 1 is a schematic view showing an ionization vapor deposition apparatus used for the manufacturing of a stent according to a first embodiment of the present invention.

21 Plasma Generator
22 Target

BEST MODE FOR CARRYING OUT THE INVENTION

A medical device according to the present invention includes a diamond-like thin film (DLC film) covering the surface of a medical device body, and containing silicon (Si). The DLC film has a Si concentration which is higher in the interface thereof with the medical device body than in the surface thereof. In addition, the Si concentration continuously varies between the interface with the medical device body and the surface.

In the DLC film, carbon atoms are primarily bonded to each other as SP3 bonds which are diamond bonds and SP2 bonds which are graphite bonds. When the ratio of the SP3 bonds increases, the crystallinity increases to increase abrasive resistance and the like. When the ratio of the SP2 bonds increases, the crystallinity deteriorates to improve adhesion and the like. When Si is added into the DLC film, the bonds between the individual carbon atoms are disturbed so that the ratio of the SP3 bonds lowers to increase the ratio of the SP2 bonds.

Therefore, the DLC film of the medical device of the present invention in which the Si concentration is high in the interface thereof with the medical device body, and low in the surface thereof is excellent in adhesion on the side closer to the medical device body, while it is harder and improved in abrasive resistance, corrosive resistance, and the like with approach toward the surface thereof. In particular, in the medical device according to the present invention, the Si concentration in the DLC film continuously varies so that the characteristics of the DLC film also continuously vary, and delamination or the like is less likely to occur. It is to be noted that the Si concentration need not necessarily change at a constant rate provided that the variation of the Si concentration is continuous. The Si concentration may also temporarily increase, and decrease thereafter.

The medical device body serving as the base material of the DLC film is preferably an in-vivo indwelling medical device such as a stent, a catheter, a guide wire, a stent, a pacemaker lead, or an injection needle. The effect achieved by forming the DLC film is also high in a medical device of which hardness is required, such as a scalpel. Further, the formation of the DLC film is also preferred in a medical device in contact with a living body, blood, and the like, such as a vacuum blood collection tube, an infusion bag, a prefilled syringe, or a wound protector which is a cover patch member for wound protection because it improves the abrasive resistance, corrosive resistance, and the like.

In the case of, e.g., a stent, the material, shape, size, and the like of a stent body are not particularly limited, and a typical known stent can be used. For example, it is possible to use a stent formed by cutting a metal tube made of stainless steel, a nickel-titanium (Ni—Ti) alloy, a copper-aluminum-manganese (Cu—Al—Mn) alloy, tantalum, a cobalt-chromium (Co—Cr) alloy, iridium, an iridium oxide, niobium, or the like into a stent design using a laser, and electropolising the cut metal tube. The stent may also be formed appropriately using a method of etching a metal tube, a method of laser cutting a flat-plate metal, rounding the cut flat-plate metal, and welding it, a method of knitting a metal wire, or the like.

The material of the stent body is not limited to a metal material. The stent body may also be formed using a polymer material such as polyolefin, a polyolefin elastomer, polyamide, a polyamide elastomer, polyurethane, a polyurethane elastomer, polyester, a polyester elastomer, polyimide, polyamideimide, or polyether ether ketone, or an inorganic material such as ceramics or hydroxyapatite. A method for processing the polymer material or the inorganic material into the stent does not affect the effect of the present invention. Any processing method appropriate for an individual material can be selected arbitrarily. It is also possible to use a medical device obtained by similarly processing an arbitrary material using an arbitrary method as another medical device other than the stent.

It has been found that the adhesion between the medical device body and the DLC film can be further improved by maintaining the surface roughness of the medical device body within a given range. When the surface roughness at the surface of the medical device body is excessively small, an anchor effect exerted by the thin film on the surface of the base material decreases to degrade the adhesion between the medial device body and the DLC film. To reduce the surface roughness, prolonged electropolising is required to result in high cost. It is possible to achieve a cost reduction by increasing the surface roughness and thereby reducing an electropolising time but, when the surface roughness at the surface of the medical device body is larger then the thickness of the DLC film, the DLC may not be formed uniformly. Accordingly, it is appropriate to set the arithmetical mean surface roughness (Ra) at the surface of the medical device body to a value of not less than 0.1 nm and not more than 300 nm, or preferably not less than 1 nm and not more than 200 nm.

The DLC film can be formed on the surface of the medical device body by a known method such as a sputter method, a DC magnetron sputter method, an RF magnetron sputter method, a chemical vapor deposition method (CVD method), a plasma CVD method, a plasma based ion implantation method, a plasma based ion implantation method applying RF and plus bias, an ion plating method, an arc ion plating method, an ion beam evaporation method, or a laser ablation method.

By adding a gas serving as a silicon source such as tetramethylsilane (TMS) during the formation of the DLC film, and continuously varying the amount of the added gas, it is possible to obtain the DLC film containing Si, and having a Si concentration which continuously varies from the interface thereof with the medical device body toward the surface thereof. However, when the Si concentration is excessively high, the ratio of the SP3 bonds lowers so that the DLC film does not function as such any more. Therefore, the atomic percent concentration of Si in the portion having a highest silicon concentration is preferably adjusted to be not more than 50%. Preferably, the Si concentration is adjusted to be highest in the interface with the medical device body in terms of improved adhesion. To further ensure the abrasive resistance of the surface, the Si concentration is adjusted to be lower in the surface than in the interface with the medical device body. Preferably, the Si concentration in the surface is adjusted to be lower by 10% or more of the Si concentration in the portion having the highest concentration to form a concentration gradient.

By varying the Si concentration in the DLC film, the ratio between the SP2 bonds and the SP3 bonds relative to the bonds between the carbon atoms in the DLC film is varied. Accordingly, the abundance ratio of the SP2 bonds to the SP3 bonds in the DLC film becomes higher in the interface with the medical device body than in the surface.

By the variation in the ratio between the SP2 bonds and the SP3 bonds, the elastic modulus (Young's modulus) of the DLC film is also varied. Because the ratio of the SP3 bonds is high in the surface of the DLC film, the Young's modulus is higher than in the interface with the medical device body. The Young's modulus at the surface of the DLC film is set appropriately to a value of not less than 50 GPa and not more than 400 GPa, or preferably not less than 80 GPa and not more than 300 Pa.

In terms of preventing the degradation of the medical device body by a biological component, the thickness of the DLC film is preferably larger. However, in the case of a device to which significant deformation is added during the use thereof, such as a stent, a crack may occur during the deformation when the thickness of the DLC film is excessively enlarged. Accordingly, the thickness of the DLC film is set appropriately to a value of not less than 5 nm and not more than 300 nm, or preferably not less than 10 nm and not more than 100 nm.

Although the DLC film can be formed directly on the surface of the medical device body, an intermediate layer may also be provided between the medical device body and the DLC film to more solidly adhere the DLC film to the medical device body. In the case of providing the intermediate layer, various intermediate layers can be provided in accordance with the material of the medical device body, and a known intermediate layer such as an amorphous film made of Si and carbon, titanium (Ti) and carbon, or chromium (Cr) and carbon can be used.

Because the intermediate layer needs to be uniformly formed on the surface of the medial device body, it requires a certain magnitude of film thickness. However, when the film thickness is excessively large, a film deposition time is elongated to degrade productivity. Accordingly, the film thickness of the intermediate layer is set appropriately to a value of not less than 5 nm and not more than 100 nm, or preferably not less than 10 nm and not more than 40 nm.

The intermediate layer can be formed using a known method. For example, a sputter method, a CVD method, a plasma CVD method, a flame spraying method, an ion plating method, an arc ion plating method, or the like may be used appropriately.

To improve an anti-thrombotic property by rendering the surface of the DLC film hydrophobic, fluorine may also be further added to the DLC film. In this case, as the amount of added fluorine is larger, a further improvement in anti-thrombotic property can be expected, but hardness may be reduced by the addition of fluorine to degrade mechanical abrasive resistance. Accordingly, the content of fluorine in the surface of the DLC film is set appropriately to a value of not less than 1 atomic percent (at %) and not more than 20 at %, or preferably not less than 5 at % and not more than 15 at %. In this case, it is preferable that the fluorine concentration of the DLC film increases continuously from the side closer to the medical device body toward the surface. This is for preventing the degradation of the adhesion between the medical device body and the DLC film by the addition of fluorine.

The medical device according to the present invention will be described hereinbelow in greater detail with the embodiments thereof.

Embodiment 1

The medical device according to the first embodiment of the present invention is a stent, and a stent body was formed as follows. First, a Co—Cr alloy material was mold-processed into a tube shape by cold working and heat treatment. The mold-processed tube was processed into a mesh shape by laser microfabrication after optimizing the physical properties of the stent, such as radial force, flexibility, shortening, and stress-strain, and the shape thereof by applying specific shape design software based on a genetic algorithm. To the stent processed into the mesh shape using a laser, electropolishing was performed for the deburring of the processed surface. In the present embodiment, the stent with the stent body made of a Co—Cr alloy and having a length of 19 mm, a diameter of 1.5 mm, and a cell thickness of 75 μm was manufactured.

FIG. 1 schematically shows an ionization vapor deposition apparatus used in the present embodiment. The ionization vapor deposition apparatus is a typical ionization vapor deposition apparatus which generates a plasma by introducing Ar and a benzene ($C_6H_6$) gas, each as an ion source, into a DC arc discharge plasma generator 21 provided within a vacuum chamber, and causes the generated plasma to collide with a target 22 biased with a negative voltage to solidify and form a DLC film on the target 22.

Bombard cleaning was performed for about 30 minutes by setting the stent body in the chamber of the ionization vapor deposition apparatus, introducing an argon gas (Ar) into the chamber to provide a pressure of $10^{-1}$ Pa to $10^{-3}$ Pa ($10^{-3}$ Torr to $10^{-5}$ Torr), generating Ar ions by performing discharge, and then causing the generated Ar ions to collide with the surface of the stent body.

Subsequently, tetramethylsilane ($Si(CH_3)_4$) was introduced into the chamber for three minutes to form an amorphous intermediate layer containing silicon (Si) and carbon (C) as main components, and having a film thickness of 10 nm. It is to be noted that the intermediate layer was provided to improve the adhesion between the stent body and the DLC film, and may also be omitted when sufficient adhesion can be ensured between the stent body and the DLC film 12.

After the intermediate layer was formed, the DLC film containing Si was formed by performing discharge, while introducing a gas mixture of tetramethylsilane and a $C_6H_6$ gas into the chamber. The mixture ratio between tetramethylsilane and the $C_6H_6$ gas was varied with the lapse of a film deposition time, as shown in Table 1.

TABLE 1

| Time (Minute) | Mixture Ratio Tetramethylsilane:Benzene |
|---|---|
| 0 to 3 | 5:5 |
| 3 to 6 | 4:6 |
| 6 to 9 | 3:7 |
| 9 to 12 | 2:8 |
| 12 to 15 | 1:9 |

In this case, the pressure in the chamber was adjusted to be $10^{-1}$ Pa. A substrate voltage was set to 1.5 kV, a substrate current was set to 50 mA, a filament voltage was set to 14 V, a filament current was set to 30 A, an anode voltage was set to 50 V, an anode current was set to 0.6 A, a reflector voltage was set to 50 V, and a reflector current was set to 6 mA. The temperature of the stent body during the formation was about 160° C. It is also possible to form a DLC film containing Si and fluorine by adding a gas containing fluorine such as $CF_4$ thereto during the formation of the DLC film.

The results of performing various analyses on the obtained stent will be shown hereinbelow. As a comparative example, a stent having a DLC film formed without the supply of tetramethylsilane was used.

A stent is a medical device used to stretch open a blocked portion of a tubular organ such as a blood vessel by being expanded therein. For example, in the case of a stent used in a coronary artery having a largest number of operation examples, the stent having a diameter of about 1.0 mm to 1.5 mm before expansion is expanded to have a diameter of about 3.0 mm to 4.0 mm in the blood vessel. As a result, distortion occurring in the stent during the expansion locally reaches about 30% so that, when the DLC film has poor adhesion, it easily delaminates.

FIGS. 2(a) and 2(b) show the result of observing the surface state when each of the obtained stents was expanded using a scanning electron microscope (SEM). The observation was performed with respect to a portion where largest distortion bad occurred by numerical analysis.

As shown in FIG. 2(a), the surface of the stent of the present embodiment was extremely smooth even though the expansion was performed, and the occurrence of a crack or the like was not observed. By contrast, as shown in FIG. 2(b), a scale-like pattern resulting from the occurrence of a large number of fine cracks was observed in the stent of the comparative example having the DLC film formed without the supply of tetramethylsilane, and it is obvious that the DLC film is likely to delaminate.

Figure 3:
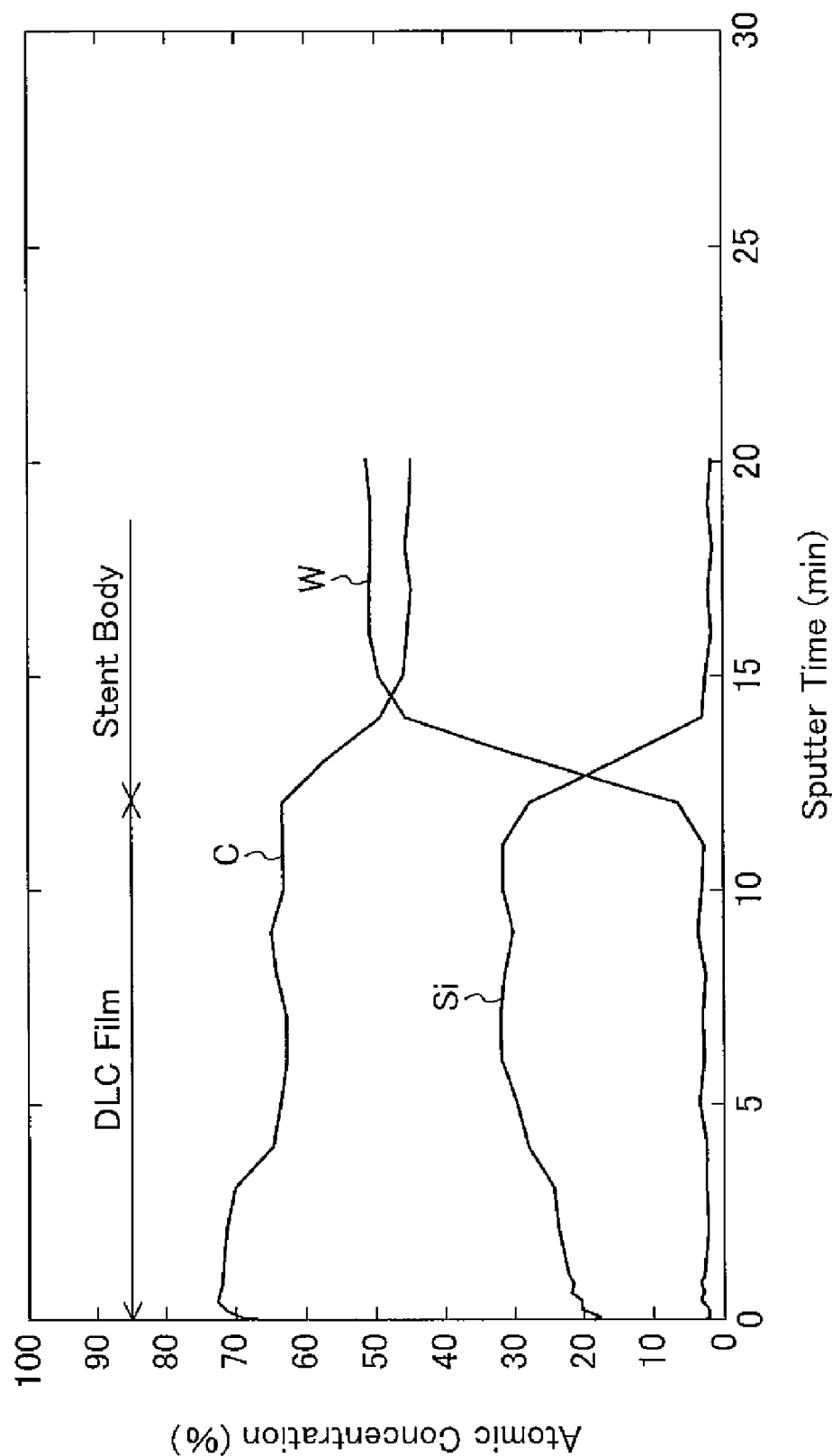
FIG. 3 shows the result of Auger electron spectroscopic analysis which shows a component variation in the direction of depth of the stent according to the first embodiment of the present invention.

FIG. 3 shows the result of analyzing the constituent components of the obtained stent. For measurement, a PHI-660 scanning Auger microscope commercially available from PHYSICAL ELECTRONICS Inc. was used. The measurement was performed under conditions such that the acceleration voltage of an electron gun was 10 kV, and a sample current was 500 nA. The acceleration voltage of an Ar ion gun was set to 2 kV, and a sputtering rate was set to 8.2 nm/min.

As shown in FIG. 3, the value of the atomic percent (at %) of Si gradually increases from the surface of the DLC film toward the side closer to the stent body, while the value of the atomic percent of carbon gradually decreases from the surface of the DLC film toward the side closer to the stent body. This indicates that the concentration of Si contained in the DLC film continuously varies to be high in the interface thereof with the stent body, and low in the surface thereof.

Figure 4:
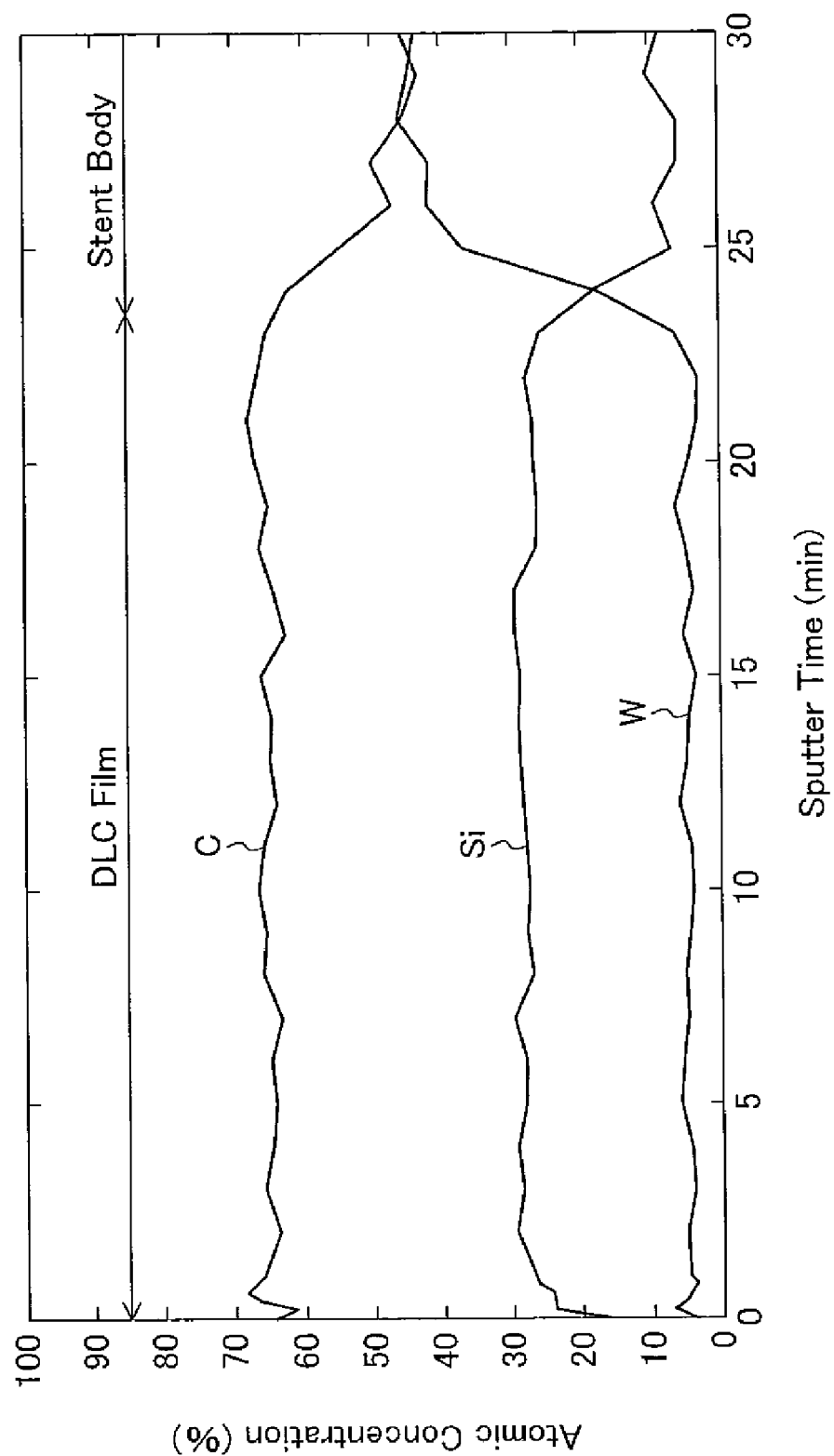
FIG. 4 shows the result of Auger electron spectroscopic analysis which shows a component variation in the direction of depth of the stent according to the comparative example of the first embodiment of the present invention.

FIG. 4 shows the result of performing measurement with respect to a DLC film formed by supplying a $C_6H_6$ gas and tetramethylsilane under different conditions. Thus, it is also possible to increase the variation in Si concentration in the vicinity of the surface of the DLC film.

Figure 5:
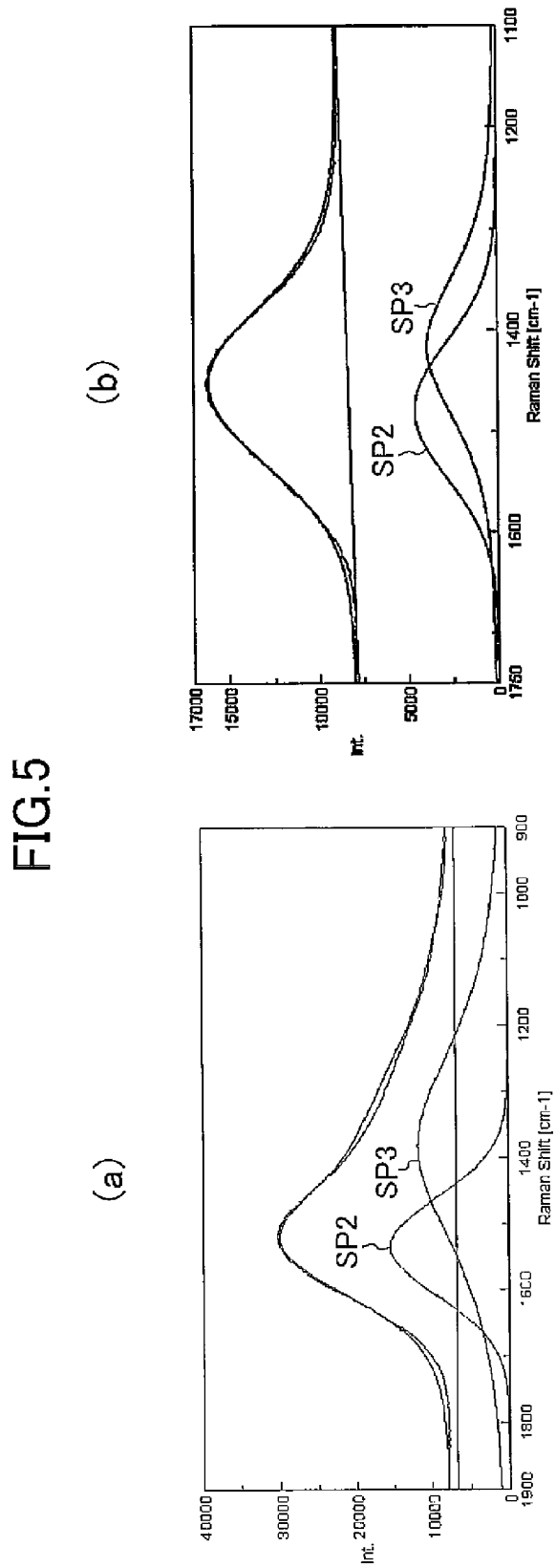

FIG. 5 show the result of measuring a crystal structure of a carbon atom for the DLC film of the obtained stent. For the measurement, an NRS-3200 laser Raman microspectrophotometer commercially available from JASCO Corporation was used. An excitation wavelength was set to 532 nm, a laser power was set to 10 mW, the grating used was 600 lines/mm, the magnification of an objective lens was set to 20, the size of a slit was set to 0.1×6 mm, an exposure time was set to 60 seconds, and integration was performed twice.

As shown in FIG. 5(a), a peak area showing diamond bonds (SP3 bonds) is larger than a peak area showing graphite bonds (SP2 bonds) at the surface of the DLC film. On the other hand, as shown in FIG. 5(b), a peak area showing the SP2 bonds is larger than a peak showing the SP3 bonds at the interface thereof with the stent body.

As a result of determining the abundance ratio between the SP2 bonds and the SP3 bonds by determining the individual peak areas by a curve fitting process (band decomposition), and determining the ratio between the obtained peak areas, the abundance ratio of the SP2 bonds to the SP3 bonds in the interface with the stent body was 0.46, and the abundance ratio of the SP2 bonds to the SP3 bonds in the surface was 1.17. That is, in the interface with the stent body having a high Si concentration, the number of the diamond bonds is smaller and the number of the graphite bonds is larger than in the surface. This indicates that the hardness of the DLC film is lower in the interface with the stent body than in the surface.

As a result of actually measuring the hardness of the DLC film, and the Young's modulus thereof, the hardness was 26 GPa and the Young's modulus was 113 GPa at the interface with the stent body having a high Si concentration, while the hardness was 29 GPa and the Young's modulus was 210 GPa at the surface having a low Si concentration.

The measurement of the hardness and the Young's modulus was performed by a nano-indentation method using a diamond penetrator in the shape of a 90-degree triangular pyramid in which a sensor with a high sensitivity (0.0004 nm, 3 nN) commercially available from Hysitron, Inc. was mounted. For the measurement of the state of an imprint, a scanning probe microscope (SPM: Scanning Probe Microscope) commercially available from Shimadzu Corporation which allows high-magnification observation of a three-dimensional shape by scanning the surface of a sample with an extremely fine probe needle was used. The diamond penetrator was pressed into the sample, while it was controlled with the accuracy of 100 μN as a condition for the measurement by the nano-indentation, and dynamic properties such as hardness and elastic modulus were quantitatively determined from the analysis of a load-displacement curve. The measurement was performed by setting a penetrator insertion time to 5 seconds, and also setting an extraction time to 5 seconds.

Figure 6:
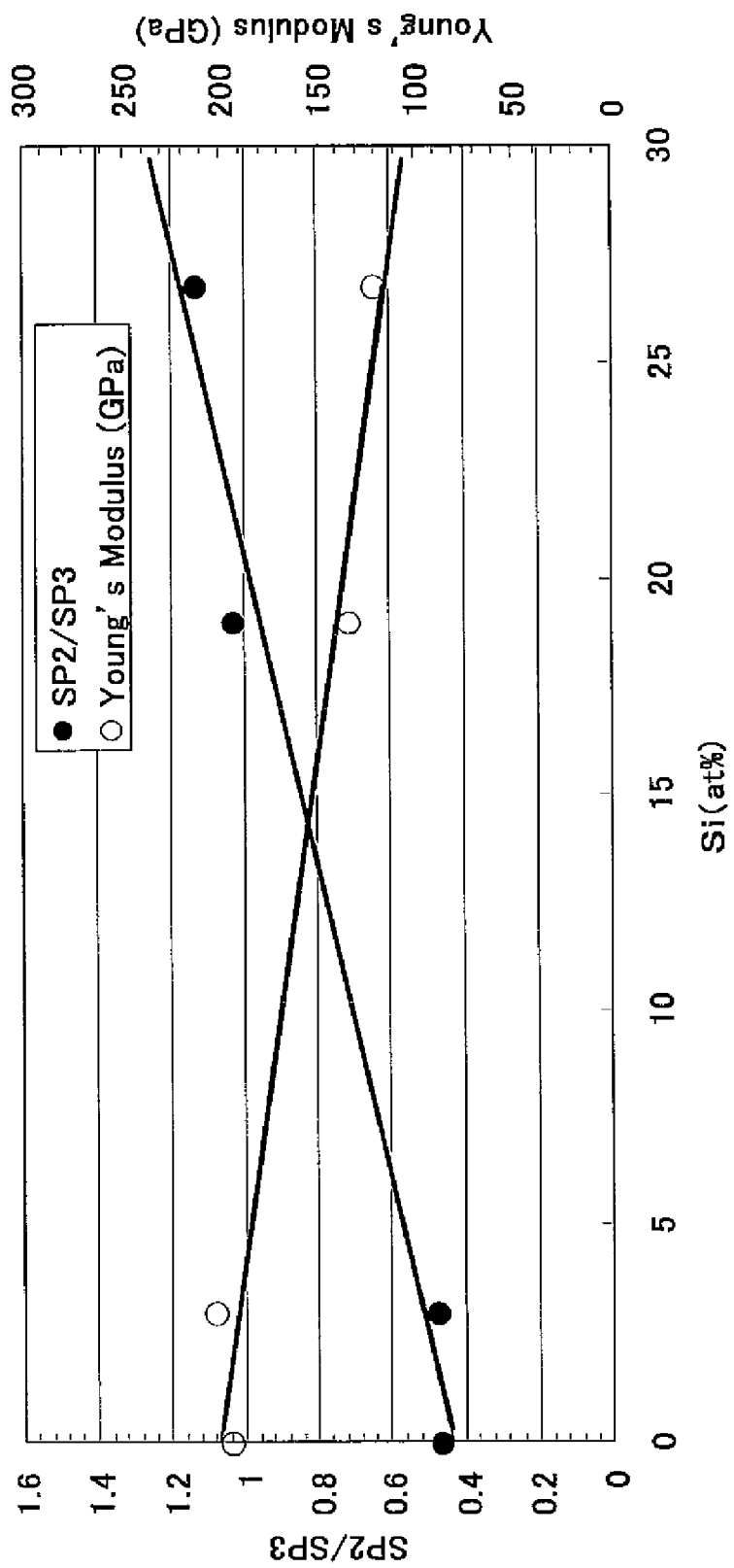
FIG. 6 is a graph showing the correlations among a Young's modulus, the abundance ratio of the SP2 bonds to the SP3 bonds, and a silicon concentration in the DLC film of the stent according to the first embodiment of the present invention.

FIG. 6 shows the correlations among a Si concentration, the abundance ratio of the SP2 bonds to the SP3 bonds, and a Young's modulus in the DLC film of the obtained stent. As shown in FIG. 6, as the Si concentration is higher, the ratio of the SP2 bonds to the SP3 bonds increases, and the value of the Young's modulus also decreases. This indicates that the crystallinity of the DLC film is lower and the adhesion between the DLC film and the stent body is improved in the interface of the DLC film with the stent body where the Si concentration is high, while the crystallinity of the DLC film increases, the hardness is high, and the abrasive resistance is excellent in the surface thereof where the Si concentration is low.

As a result of performing an external accelerated fatigue test with respect to the actually obtained stents, each of the stents was proved to have excellent durability. The test was performed with respect to the sixteen stents by a method as shown below in accordance with "FDA Draft Guidance for the Submission of Research and Marketing Applications for Interventional Cardiology Devices" issued by the American Food and Drug Administration (FDA), which is a test standard related to the durability of a stent used for a coronary artery.

First, the stent was expanded to a diameter of 3.0 mm in a tube made of latex having an outer diameter of about 3.5 mm and a thickness of about 0.5 mm. In a state where the tube made of latex in which the stent was allowed to dwell was immersed in a physiological saline at 37±2° C., expansion and compression was added in a radial direction to the tube four hundreds of millions of times. For the expansion and compression, pressure variations ranging from a minimum value of 80 mmHg to a maximum value of 160 mmHg corresponding to the pulsation of a heart were added at a speed of sixty times per minute.

After the completion of the test, the presence or absence of cracks was visually observed using a 10-magnification microscope. In addition, the outer shape of the tube was measured using a laser displacement gage to measure the presence or absence of a significant reduction in the outer diameter of the tube due to the collapse of each of the stents.

As shown in Table 2, the occurrence of cracks was not recognized in the DLC films of all the stents. The outer diameters of the tubes of all the sixteen test samples did not substantially vary, and the collapse of the stents did not occur, either. Thus, it is obvious that each of the stents having the DLC film according to the present embodiment has excellent durability.

TABLE 2

| No. | Mean Outer Diameter | Crack |
| --- | --- | --- |
| 1 | 4.64 | None |
| 2 | 4.70 | None |
| 3 | 4.62 | None |
| 4 | 4.62 | None |
| 5 | 4.64 | None |
| 6 | 4.63 | None |
| 7 | 4.67 | None |
| 8 | 4.64 | None |
| 9 | 4.68 | None |
| 10 | 4.67 | None |
| 11 | 4.61 | None |
| 12 | 4.60 | None |
| 13 | 4.68 | None |
| 14 | 4.76 | None |
| 15 | 4.57 | None |
| 16 | 4.61 | None |
| Average | 4.65 | None |

Embodiment 2

A description will be given hereinbelow to a second embodiment of the present invention. A medical device according to the second embodiment is a guide wire for a catheter for percutaneous coronary artery plasty.

A DLC film containing Si was formed on a guide wire body made of stainless steel and having a diameter of 0.25 mm by the same method as used in the first embodiment.

The durability of the guide wire having the obtained DLC film was measured as follows.

A U-shaped tube having a radius of 13 mm was formed by bending a polyethylene tube having an outer diameter of 2.9 mm, an inner diameter of 2.3 mm, and a length of 500 mm at the center portion thereof and the tube was internally filled with ion exchanged water. The guide wire was inserted into the U-shaped tube, the end portion thereof was extracted at a speed of about 1 m/minute, and a load at the time of extraction was measured using a spring balance. The value of the load barely changed even when the extraction of the guide wire was repeated twenty times or more, and a smoothing effect achieved by the DLC film lasted. Therefore, it is obvious that the guide wire of the present embodiment has the DLC film which is excellent in adhesion and abrasive resistance, and has excellent lubricity and durability.

The guide wire of the present embodiment may also be further coated with a methyl vinyl ether-maleic anhydride copolymer (GANTREZ-GN169) which is an anti-thrombotic polymer or the like. The arrangement allows a further improvement in the anti-thrombotic property of the guide wire.

Embodiment 3

A description will be given hereinbelow to a third embodiment of the present invention. A medical device according to the third embodiment is a vacuum blood collection tube.

A DLC film containing Si was formed on a plastic vacuum blood collection tube by the same method as used in the first embodiment. A loss of vacuum in the obtained vacuum blood collection tube after it was preserved at a room temperature for one year was improved by 50% of a loss of vacuum in a vacuum blood collection tube on which a DLC film was not formed. Therefore, it is obvious that the vacuum blood collection tube of the present embodiment has the DLC film which is excellent in adhesion and durability.

INDUSTRIAL APPLICABILITY

A medical device and a method for manufacturing thereof according to the present invention allow the implementation of a medial device formed with a diamond-like thin film having both excellent adhesion which prevents the delamination thereof from the surface of the base material of the medical device over a long period of time and excellent abrasive resistance which renders the surface thereof less susceptible to degradation. Therefore, the medical device is particularly useful as a medical device of which biocompatibility, abrasive resistance, and corrosive resistance are required.

The invention claimed is:

1. A medical device comprising:
    a medical device body; and
    a diamond-like thin film covering the medical device body and containing silicon, wherein
    the diamond-like thin film has a concentration of the silicon which is present in a surface thereof and is lower in a surface thereof than in an interface thereof with the medical device body, and continuously varies, and
    the medical device body is any one of a stent, a catheter, and a guide wire
    wherein the diamond-like thin film has an elastic modulus which is larger in the surface thereof than in the interface thereof with the medical device body, and
    the diamond-like thin film has the elastic modulus which is not less than 50 GPa and not more than 400 GPa in the surface thereof.

2. The medical device of claim 1, wherein the diamond-like thin film has an atomic percent concentration of the silicon which is not more than 50% in a portion thereof having the highest silicon concentration.

3. The medical device of claim 2, wherein the diamond-like thin film has the silicon concentration which is highest in the interface thereof with the medical device body.

4. The medical device of claim 2, wherein the diamond-like thin film has the silicon concentration in the surface thereof which is not more than 90% of the silicon concentration in the portion thereof having the highest silicon concentration.

5. The medical device of claim 1, wherein the diamond-like thin film has graphite bonds and diamond bonds, and an abundance ratio of the graphite bonds to the diamond bonds is lower in the surface of the diamond-like thin film than in the interface thereof with the medical device body.

6. The medical device of claim 1, wherein the diamond-like thin film contains fluorine, and has a concentration of the fluorine which is higher in the surface thereof than in the interface thereof with the medical device body, and continuously varies.

7. The medical device of claim 6, wherein the diamond-like thin film has an atomic percent concentration of the fluorine which is not less than 1% and not more than 20% in the surface thereof.

8. The medical device of claim 1, wherein the diamond-like thin film has a film thickness which is not less than 5 nm and not more than 300 nm.

9. The medical device of claim 1, wherein the medical device body has an arithmetical mean surface roughness which is not less than 0.1 nm and not more than 300 nm in a surface thereof.

10. The medical device of claim 1, wherein the medical device body is a composite made of one or two or more of a metal material, a ceramics material, and a polymer material.

11. The medical device of claim 10, wherein the metal material is stainless steel, a cobalt-chromium alloy, a titanium alloy, or a cobalt alloy.

12. A method for manufacturing a medical device, the method comprising the steps of:
(a) preparing a medical device body; and
(b) forming a diamond-like thin film containing silicon on a surface of the medical device body, wherein,
in the step (b), the diamond-like thin film is formed to have a concentration of silicon which is present in a surface thereof and is lower in a surface thereof than in an interface thereof with the medical device body, and continuously varies, and an atomic percent concentration of the silicon which is not more than 50% in a portion thereof having the highest silicon concentration, and
in the step (a), any one of a stent, a catheter, and a guide wire is prepared as the medical device body.

13. The method for manufacturing a medical device of claim 12, wherein, in the step (b), the diamond-like thin film is formed to have the silicon concentration which is highest in the interface thereof with the medical device body.

14. The method for manufacturing a medical device of claim 12, wherein, in the step (b), the diamond-like thin film is formed to have the silicon concentration in the surface thereof which is not more than 90% of the silicon concentration in the portion thereof having the highest silicon concentration.

15. The method for manufacturing a medical device of claim 12, wherein, in the step (b), the diamond-like thin film is formed to have an elastic modulus which is larger in the surface thereof than in the interface thereof with the medical device body.

16. The method for manufacturing a medical device of claim 12, wherein, in the step (b), the diamond-like thin film is formed to have graphite bonds and diamond bonds such that an abundance ratio of the graphite bonds to the diamond bonds is lower in the surface of the diamond-like thin film than in the interface thereof with the medical device body.

17. The method for manufacturing a medical device of claim 12, wherein, in the step (b), the diamond-like thin film is formed to contain fluorine, and have a concentration of the fluorine which is higher in the surface thereof than in the interface thereof with the medical device body, and continuously varies.

18. A medical device comprising:
a medical device body; and
a diamond-like thin film covering the medical device body and containing silicon, wherein
the diamond-like thin film has a concentration of the silicon which is present in a surface thereof and is lower in a surface thereof than in an interface thereof with the medical device body, and continuously varies, and
the medical device body is any one of a stent, a catheter, and a guide wire
wherein the medical device body has an arithmetical mean surface roughness which is not less than 0.1 nm and not more than 300 nm in a surface thereof.

19. The medical device of claim 18, wherein the diamond-like thin film has an atomic percent concentration of the silicon which is not more than 50% in a portion thereof having the highest silicon concentration.

20. The medical device of claim 19, wherein the diamond-like thin film has the silicon concentration which is highest in the interface thereof with the medical device body.

21. The medical device of claim 19, wherein the diamond-like thin film has the silicon concentration in the surface thereof which is not more than 90% of the silicon concentration in the portion thereof having the highest silicon concentration.

22. The medical device of claim 18, wherein the diamond-like thin film has an elastic modulus which is larger in the surface thereof than in the interface thereof with the medical device body.

23. The medical device of claim 22, wherein the diamond-like thin film has the elastic modulus which is not less than 50 GPa and not more than 400 GPa in the surface thereof.

24. The medical device of claim 18, wherein the diamond-like thin film has graphite bonds and diamond bonds, and an abundance ratio of the graphite bonds to the diamond bonds is lower in the surface of the diamond-like thin film than in the interface thereof with the medical device body.

25. The medical device of claim 18, wherein the diamond-like thin film contains fluorine, and has a concentration of the fluorine which is higher in the surface thereof than in the interface thereof with the medical device body, and continuously varies.

26. The medical device of claim 25, wherein the diamond-like thin film has an atomic percent concentration of the fluorine which is not less than 1% and not more than 20% in the surface thereof.

27. The medical device of claim 18, wherein the diamond-like thin film has a film thickness which is not less than 5 nm and not more than 300 nm.

28. The medical device of claim 18, wherein the medical device body is a composite made of one or two or more of a metal material, a ceramics material, and a polymer material.

29. The medical device of claim 28, wherein the metal material is stainless steel, a cobalt-chromium alloy, a titanium alloy, or a cobalt alloy.

* * * * *